United States Patent [19]
LeBlanc et al.

[11] Patent Number: 6,071,954
[45] Date of Patent: Jun. 6, 2000

[54] (METHYLSULFONYL)PHENYL-2-(5H)-FURANONES WITH OXYGEN LINK AS COX-2 INHIBITORS

[75] Inventors: Yves LeBlanc, Kirkland; Patrick Roy; Serge Leger, both of Dollard Des Ormeaux; Erich Grimm, Baie D'Urfe; Zhaoyin Wang, Pierrefonds, all of Canada

[73] Assignee: Merk Frosst Canada, Inc., Kirkland, Canada

[21] Appl. No.: 09/042,168

[22] Filed: Mar. 13, 1998

Related U.S. Application Data

[60] Provisional application No. 60/040,794, Mar. 14, 1997.
[51] Int. Cl.[7] .................. A61K 31/365; C07D 307/60
[52] U.S. Cl. ................. 514/473; 549/319; 549/313
[58] Field of Search ................. 514/473, 471, 514/462; 549/319, 313

[56] References Cited

U.S. PATENT DOCUMENTS 5,883,267  3/1999  Rossen et al. ................ 549/319

FOREIGN PATENT DOCUMENTS

| 0 754 687 A1 | 1/1997 | European Pat. Off. . |
|---|---|---|
| WO 96/08482 | 3/1996 | WIPO . |
| WO 96/19649 | 6/1996 | WIPO . |
| WO 97/14691 | 4/1997 | WIPO . |
| WO 97/16435 | 5/1997 | WIPO . |
| WO 97/28121 | 8/1997 | WIPO . |
| WO 97/45420 | 12/1997 | WIPO . |

OTHER PUBLICATIONS

Patent Abstracts of Japan vol. 17, No. 361 (1993).

*Primary Examiner*—John Kight
*Assistant Examiner*—Charanjit S. Aulakh
*Attorney, Agent, or Firm*—Richard C. Billups; David L. Rose

[57] ABSTRACT

The invention encompasses the novel compound of Formula I useful in the treatment of cyclooxygenase-2 mediated diseases.

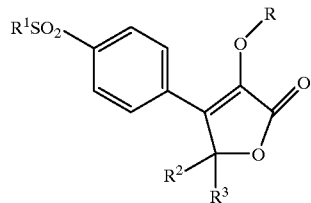

The invention also encompasses certain pharmaceutical compositions for treatment of cyclooxygenase-2 mediated diseases comprising compounds of Formula I.

13 Claims, No Drawings

(METHYLSULFONYL)PHENYL-2-(5H)-FURANONES WITH OXYGEN LINK AS COX-2 INHIBITORS

CROSS REFERENCE TO RELATED APPLICATIONS

This application is based upon Provisional Application No. 60/040,794 filed on Mar. 14, 1997, priority of which is claimed hereunder.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

A brief description of the potential utility of cyclooxygenase-2 inhibitors is given in an article by John Vane, Nature, Vol. 367, pp. 215–216, 1994, and in an article in Drug News and Perspectives, Vol. 7, pp. 501–512, 1994.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

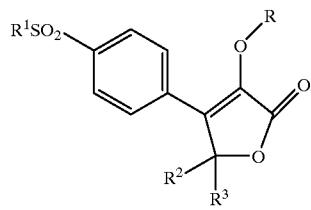

The invention also encompasses certain pharmaceutical compositions for treatment of cyclooxygenase-2 mediated diseases comprising compounds of Formula I.

DETAILED DESCRIPTION OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

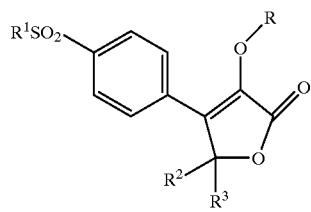

wherein:

R is a mono-, di- or tri-substituted $C_{1-12}$alkyl, or a mono-, or an unsubstituted or mono-, di- or tri-substituted linear or branched $C_{2-10}$alkenyl, or an unsubstituted or mono-, di- or tri-substituted linear or branched $C_{2-10}$alkynyl, or an unsubstituted or mono-, di- or tri-substituted $C_{3-12}$cycloalkenyl, or an unsubstituted or mono-, di- or tri-substituted $C_{5-12}$cycloalkynyl, wherein the substituents are chosen from the group consisting of
(a) halo, selected from F, Cl, Br, and I,
(b) OH,
(c) $CF_3$,
(d) $C_{3-6}$cycloalkyl,
(e) =O,
(f) dioxolane,
(g) CN and $R^1$ is selected from the group consisting of
(a) $CH_3$,
(b) $NH_2$,
(c) $NHC(O)CF_3$,
(d) $NHCH_3$;

$R^2$ and $R^3$ are independently chosen from the group consisting of
(a) hydrogen,
(b) $C_{1-10}$loalkyl, or $R^2$ and $R^3$ together with the carbon to which they are attached form a saturated monocyclic carbon ring of 3, 4, 5, 6 or 7 atoms.

A preferred embodiment of this invention is that wherein R is a mono-, di-, or tri-substituted linear or branched $C_{1-10}$ alkyl or a mono-, di-, or tri-substituted $C_{3-12}$ cycloalkyl.

Another preferred embodiment is that wherein the substituent on R is halo.

Another preferred embodiment is that wherein $R^2$ and $R^3$ are each methyl.

Another preferred embodiment is that wherein $R^1$ is $CH_3$ or $NH_2$.

In another aspect the invention also encompasses a pharmaceutical composition for treating an inflammatory disease susceptable to treatment with an non-steroidal anti-inflammatory agent comprising:
  a non-toxic therapeutically effective amount of a compound of formula I and a pharmaceutically acceptable carrier.

In another aspect the invention also encompasses a pharmaceutical composition for treating cyclooxygenase mediated diseases advantageously treated by an active agent that selectively inhibits COX-2 in preference to COX-1 comprising:
  a non-toxic therapeutically effective amount of a compound of formula I and a pharmaceutically acceptable carrier.

In another aspect the invention also encompasses a method of treating an inflammatory disease susceptible to treatment with an non-steroidal anti-inflammatory agent comprising:
  administration to a patient in need of such treatment of a non-toxic therapeutically effective amount of a compound of formula I and a pharmaceutically acceptable carrier.

In another aspect the invention also encompasses a method of treating cyclooxygenase mediated diseases advantageously treated by an active agent that selectively inhibits COX-2 in preference to COX-1 comprising:
  administration to a patient in need of such treatment of a non-toxic therapeutically effective amount of a compound of formula I.

In another aspect the invention also encompasses the use of a compound of formula I or a pharmaceutical composition in the manufacture of a medicament for the treatment of an inflammatory disease susceptible to treatment with a non-steroidal anti-inflammatory agent.

The invention is illustrated by the compounds of the Examples disclosed herein as well as the compounds of Table I.

1) DEFINITIONS

The following abbreviations have the indicated meanings:
AA=arachidonic acid
Ac=acetyl
CHO=chinese hamster ovary
CMC=1-cyclohexyl-3-(2-morpholinoethyl) carbodiimidemetho-p-toluenesulfonate
Cox=cyclooxygenase
DAST=diethlyaminosulfur trifluoride
DBU=diazabicyclo[5.4.0]undec-7-ene
DMAP=4-(dimethylamino)pyridine
DMF=N,N-dimethylformamide
$Et_3N$=triethylamine
HBSS=Hanks balanced salt solution
HEPES=N-[2-Hydroxyethyl]piperazine-$N^1$-[2-ethanesulfonic acid]
HWB=human whole blood
IPA=isopropyl alcohol
LPS=lipopolysaccharide
MMPP=magnesium monoperoxyphthalate
Ms=methanesulfonyl=mesyl
MsO=methanesulfonate=mesylate
NSAID=non-steroidal anti-inflammatory drug
Oxone®=potassium peroxymonosulfate
r.t.=room temperature
rac.=racemic
TBAF=tetra-n-butylammonium fluoride
Tf=trifluoromethanesulfonyl=triflyl
THF=tetrahydrofuran
TLC=thin layer chromatography
$SO_2Me$=methyl sulfone (also $SO_2CH_3$)
$SO_2NH_2$=sulfonamide

| Alkyl group abbreviations | Dose Abbreviations |
|---|---|
| Me = methyl | bid = bis in die = twice daily |
| Et = ethyl | qid = quater in die = four times a day |
| n-Pr = normal propyl | id = ter in die = three times a day |
| i-Pr = isopropyl | |
| n-Bu = normal butyl | |
| i-Bu = isobutyl | |
| s-Bu = secondary butyl | |
| t-Bu = tertiary butyl | |
| c-Pr = cyclopropyl | |
| c-Bu = cyclobutyl | |
| c-Pen = cyclopentyl | |
| c-Hex = cyclohexyl | |

For purposes of this specification "Alkyl" means linear branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0]decyl and the like.

For purposes of this specification "Fluoro alkyl" means alkyl groups in which one or more hydrogen is replaced by fluorine. Examples are $—CF_3$, $—CH_2CH_2F$, $—CH_2CF_3$, c-Pr—$F_5$, c-Hex—$F_{11}$ and the like.

For purposes of this specification "Alkoxy" means alkoxy groups of the indicated number of carbon atoms of a straight, branched, or cyclic configuration. Examples of alkoxy groups include methoxy, ethoxy, propoxy, isopropoxy, cyclopropyloxy, cyclohexyloxy, and the like.

For purposes of this specification "Alkylthio" means alkylthio groups of the indicated number of carbon atoms of a straight, branched or cyclic configuration. Examples of alkylthio groups include methylthio, propylthio, isopropylthio, cycloheptylthio, etc. By way of illustration, the propylthio group signifies $—SCH_2CH_2CH_3$.

For purposes of this specification "Halo" means F, Cl, Br, or I.

Exemplifying the invention are Examples hereinunder which include:
(1) 5,5-Dimethyl-3-((1-methylallyl)oxy)-4-(4-methylsulfonylphenyl)-5H-furan-2-one (2) 5,5-Dimethyl-3-(1,1,1,3,3,3-hexafluoropropoxy)-4-(4-methylsulfonylphenyl)-5H-furan-2-one (3) 5,5-Dimethyl-3-((1-methyl-2-propynyl)oxy)-4-(4-methylsulfonylphenyl)-5H-furan-2-one (4) 3-((1R,2S)-(1S,2R)-2-hydroxy-1-methylpropyl)oxy)-5,5-dimethyl-4-(4-methylsulfonylphenyl)-5H-furan-2-one (5) 3-((2-hydroxy-2-methyl-3-butenyl)oxy)-5,5-dimethyl-4-(4-methylsulfonyl)phenyl-5H-furan-2-one (6) 3-(2-Bromo-1-methylethoxy)-5,5-dimethyl-4-(4-methylsulfonylphenyl)-5H-furan-2-one (7) 3-(Isopropenyloxy)-5,5-dimethyl-4-(4-methylsulfonylphenyl)-5H-furan-2-one (8) 3-(((2S)-3-hydroxy-2-methylpropyl)oxy)-5,5-dimethyl-4(4-methylsulfonylphenyl)-5H-furan-2-one (9) 3-(((2R)-3-hydroxy-2-methylpropyl)oxy)-5,5-dimethyl-4-(4-methylsulfonylphenyl)-5H-furan-2-one

(10) 3-(((2R)-3-Fluoro-2-methylpropyl)oxy)-5,5-dimethyl-4-(4-methylsulfonylphenyl)-5H-furan-2-one

(11) 3-(((2S)-3-fluoro-2-methylpropyl)oxy)-5,5-dimethyl-4-(4-methylsulfonylphenyl)-5H-furan-2-one

(12) 3-(2-Hydroxy-1-methylethoxy)-5,5-dimethyl-4-(4-methylsulfonylphenyl)-5H-furan-2-one

(13) 3-(2-Fluoro-1-methylethoxy)-5,5-dimethyl-4-(4-methylsulfonylphenyl)-5H-furan-2-one

(14) 5,5-Dimethyl-4-(4-methylsulfonylphenyl)3-(2-propynyloxy)-5H-furan-2-one

(15) 3-(Allyloxy)-5,5-dimethyl-4-(4-methylsulfonylphenyl)-5H-furan-2-one

(16) 3-(1,4-dioxaspiro[4.5]dec-8-yloxy)-5,5-dimethyl-4-(4-methylsulfonylphenyl)-5H-furan-2-one

(17) 3-[(4,4-difluorocyclohexyl)oxy]-5,5-dimethyl-4(4-(methylsulfonylphenyl)-5H-furan-2-one

(18) 5,5-dimethyl-3-(2-methylallyloxy)-4-(4-(methylsulfonylphenyl)-5H-furan-2-one

(19) 5,5-Dimethyl-3-[(1-methylcyclopropyl)methoxy]-4-(4-methylsulfonylphenyl)-5H-furan-2-one

(20) 3-{[2-(fluoromethyl)allyl]oxy}-5,5-dimethyl-4-(4-methylsulfonylphenyl)-5H-furan-2-one

(21) 3-{[1-(hydroxymethyl)cyclopropyl]methoxy}-5,5-dimethyl-4-(4-methylsulfonylphenyl)-2-5H-furan-2-one

(22) 3-[(1-fluorocyclobutyl)methoxy]-5,5-dimethyl-4-(4-methylsulfonylphenyl)-5H-furan-2-one

(23) 3-{[1-(fluoromethyl)cyclopropyl]methoxy}-5,5-dimethyl-4-(4-methylsulfonylphenyl)-5H-furan-2-one

(24) 3-((2-oxocyclopentyl)oxy)-5,5-dimethyl-4-(4-methylsulfonylphenyl)-5H-furan-2-one

(25) 3-((2,2-difluorocyclopentyl)oxy-5,5-dimethyl-4-(4-methylsulfonylphenyl)-5,5-furan-2-one Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of formula I as described above.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of compound of formula I as described above.

In a third embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a patient in need of such treatment of a non-toxic therapeutically effective amount of a compound of Formula I as disclosed herein.

The pharmaceutical compositions of the present invention comprise a compound of Formula I as an active ingredient, and may also contain a pharmaceutically acceptable carrier and optionally other therapeutic ingredients.

The compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis) and for the treatment of glaucoma.

By virtue of its high cyclooxygenase-2 (COX-2) activity and/or its specificity for cyclooxygenase-2 over cyclooxygenase-1 (COX-1), Compound I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetomi-nophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo- desoxyephedrine; an antiitussive including codeine, hydrocodone, caramiphen, carbetapentane, or dextramethorphan; a prostaglandin including misoprostol, enprostil, rioprostil, ornoprostol or rosaprostol; a diuretic; a sedating or non-sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxy-ethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods Method A An appropriately substituted acid halide is reacted with thioanisole in a solvent such as chloroform in the presence of a Lewis acid such as aluminum chloride to afford a ketone which is then hydroxylated with base such as aqueous sodium hydroxide in a solvent such as carbon tetrachloride with a phase transfer agent such as Aliquat 336. Then treatment with an oxidizing agent such as MMPP in solvents such as $CH_2Cl_2/MeOH$, affords a sulfone II.

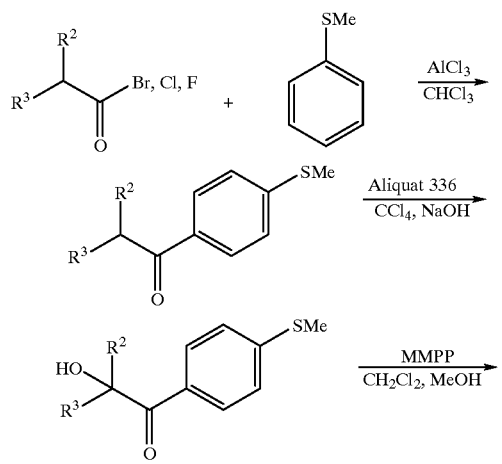

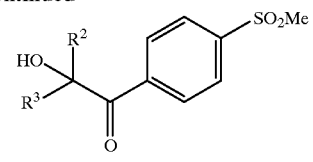

Method B

An appropriately substituted alcohol is treated with a base such as sodium hydride in a solvent such as THF and then reacted with bromo acetic acid to afford an acid III.

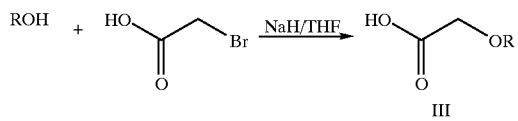

Method C

The acid of Method B (III) is reacted with an hydroxy ketone of Method A (II) with an esterifying reagent such as CMC in a solvent such as dichloromethane or benzotrifluoride to give an ester (IV) which is cyclized upon treatment with a base such as DBU in a solvent such as acetonitrile with or without isopropyl trifluoroacetate to afford I.

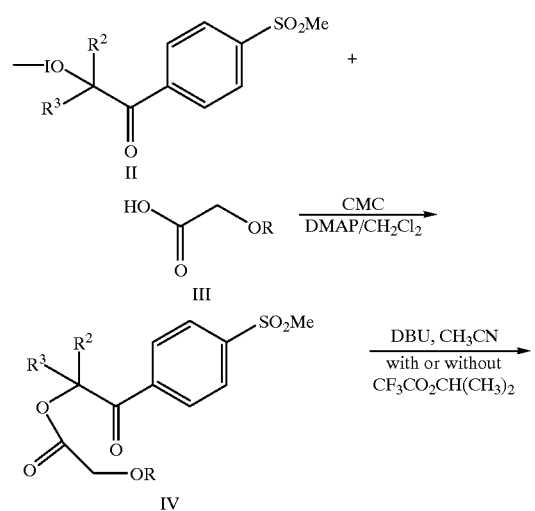

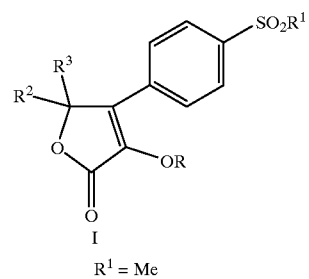

Method D

An appropriately substituted acid halide V is reacted with hydroxyketone II in the presence of a base such as pyridine in a solvent such as acetonitrile; further treatment with a base such as DBU gives a hydroxylactone VI. The hydroxylactone is reacted with an appropriately substituted halide in a solvent such as benzene with a reagent such as $Ag_2CO_3$ to afford the lactone I. Alternatively the hydroxylactone is reacted with an alkyl halide in a solvent such as DMF with reagents such as NaH, with or without $nBu_4NI$ to give I. In addition, the hydroxylactone can be reacted with an epoxide with a base such as $Et_3N$ to give I.

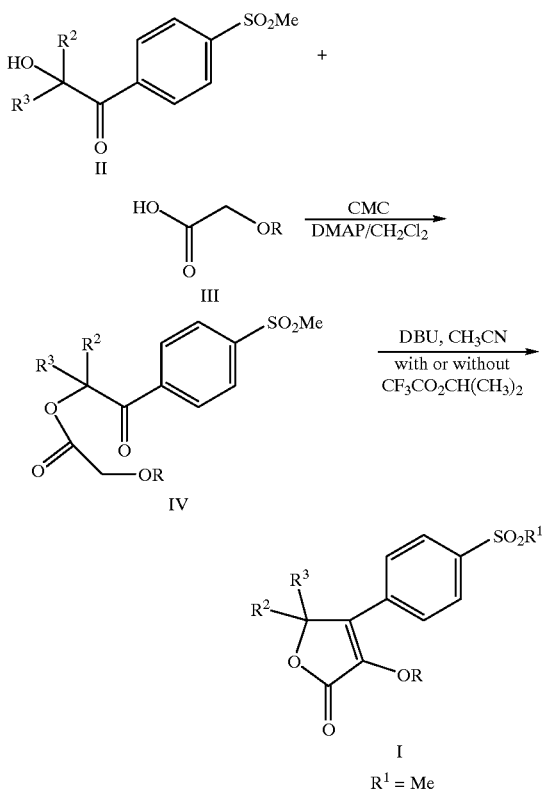

Method E

A bromide (Method Da) compound is reacted with a base such as potassium tert-butoxide to give the olefinic compound Ia.

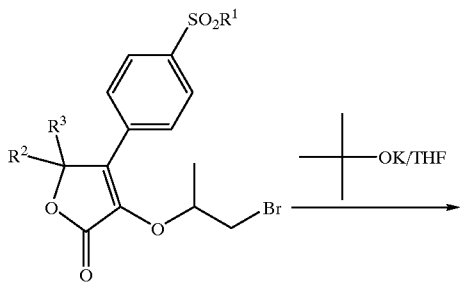

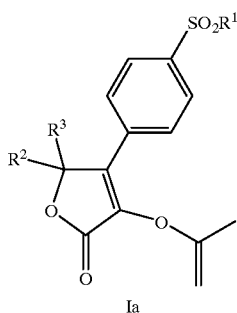

Method F

An alcohol (Method Db or Dc) is reacted with DAST in $CH_2Cl_2$ to provide the fluoro compound Ib.

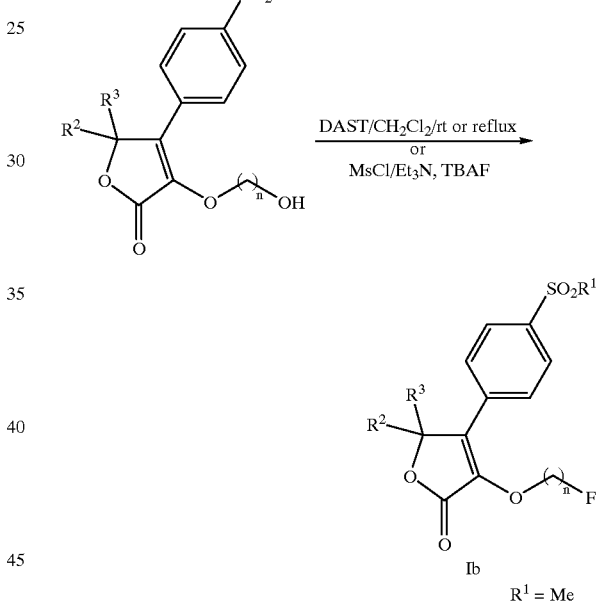

Method G

An ester (Method Da or Db) is treated with $LiBH_4$ to provide the alcohol Ic.

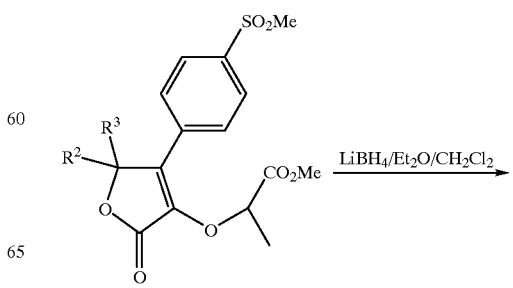

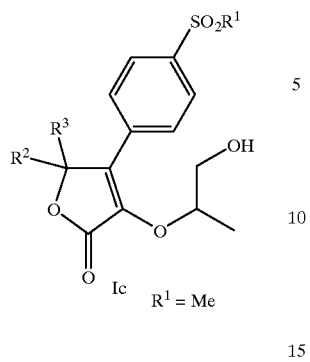

Ic  R¹ = Me

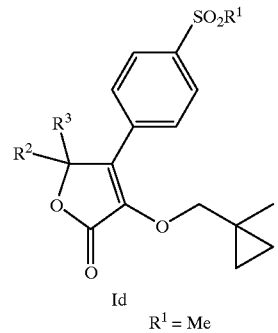

Id  R¹ = Me

Method H

A cyclodione mono-acetal is reduced with NaBH₄ and the resulting alcohol is converted to the iodide to give a mixture of the iodo acetal and iodo ketone which are separated.

Method J

To the hydroxy lactone VI (Method D) is added a dichloro olefinic compound and a base such as NaH in DMF. The mono chloro compound Ie is treated with n-Bu₄NOAc, n-Bu₄NI in CH₃CN to give the allylic alcohol If. The allylic alcohol is then converted to the fluoro analog Ig by treatment with DAST in CH₂Cl₂.

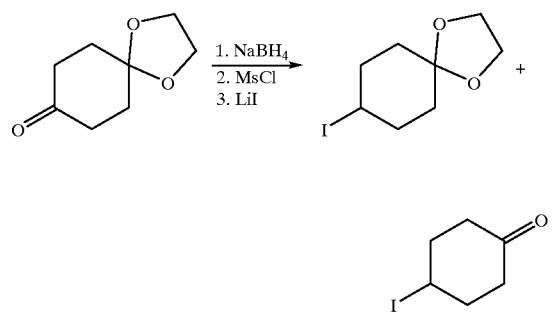

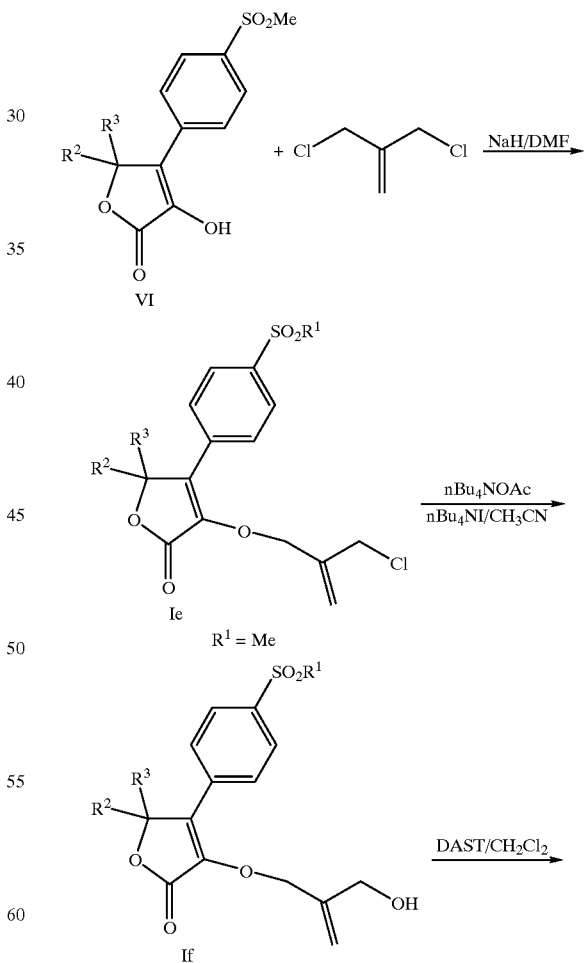

Method I

To an olefinic compound is added diethylzinc and diiodomethane to a solvent such as 1,2-dichloroethane to give the cyclopropyl compound Id.

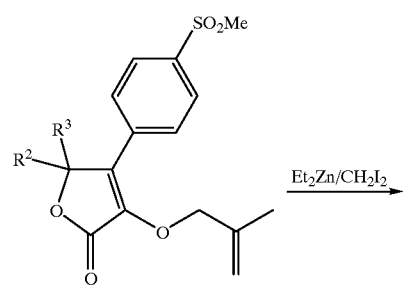

15
-continued

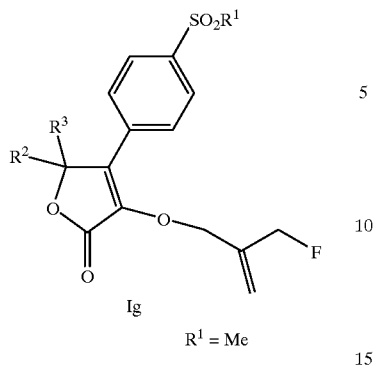

Ig
$R^1$ = Me

16
-continued

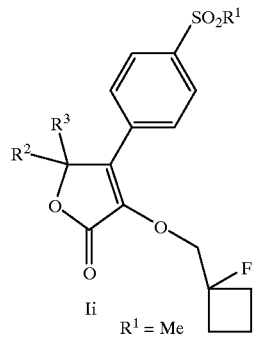

Ii  $R^1$ = Me

Method K

To the hydroxylactone VI (Method D) and a thiaspiro compound in DMF is added NaH to give the alcohol Ih.

Method M

To alcohol Ih is added MsCl and Et$_3$N in CH$_2$Cl$_2$. The mesylate is treated with nBu$_4$NF to give the fluoro compound Ij.

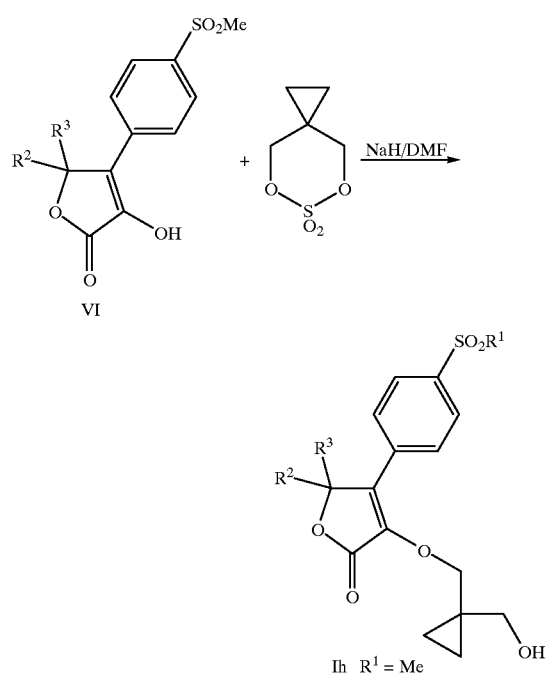

Ih  $R^1$ = Me

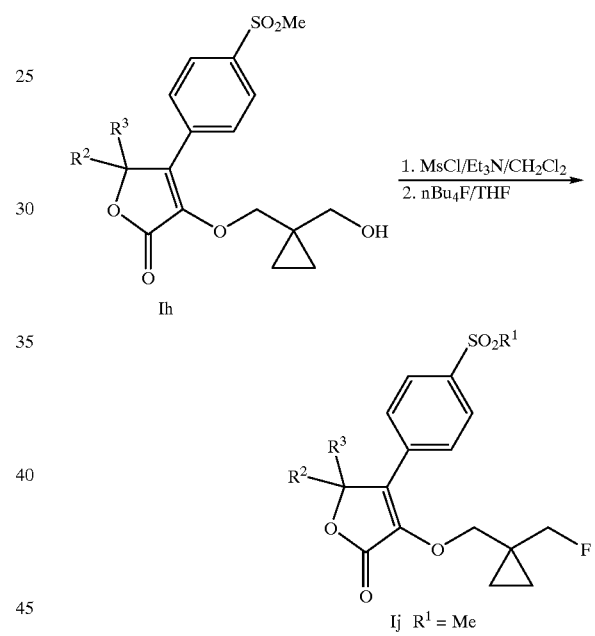

Ij  $R^1$ = Me

Method L

To alcohol Ih is added DAST to give the fluorocyclobutane compound Ii.

Method N

A ketone (from Methods H and D) is treated with DAST in a solvent such as CH$_2$Cl$_2$ or benzotrifluoride to give the difluoro compound Ik.

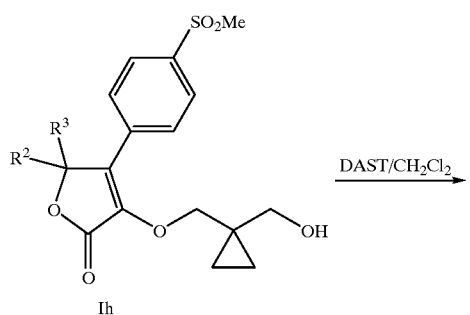

Ih

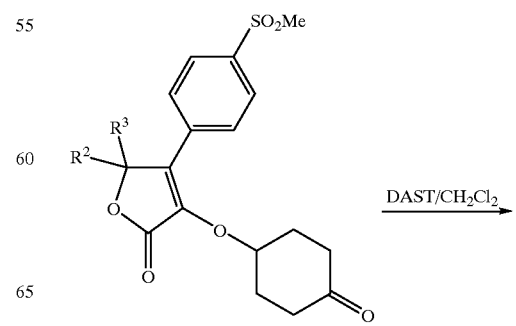

-continued
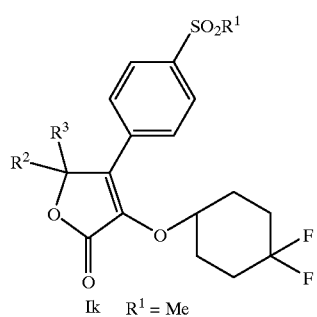
Ik    R$^1$ = Me
Representative Compounds
Table I illustrates novel compounds of the present invention.
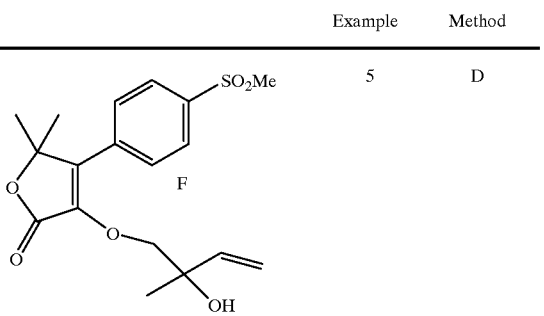

TABLE I-continued
| | Example | Method |
|---|---|---|
| 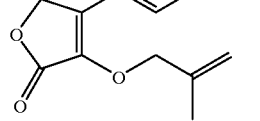 | 11 | D + F |
| 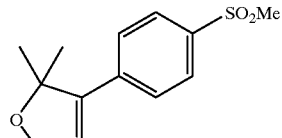 | 12 | D + G |
|  | 13 | D + G + F |
| 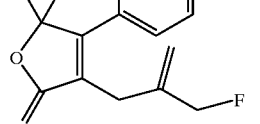 | 14 | D |
| 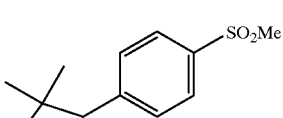 | 15 | D |
| 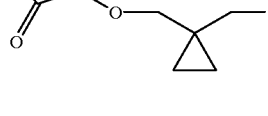 | 16 | H + D |
| | 17 | H + D + N |
| | 18 | D |
| | 19 | D + I |
| | 20 | J |
| | 21 | K |
| | 22 | K + L |
| | 23 | K + M |

TABLE I-continued

| | Example | Method |
|---|---|---|
| (structure with SO₂Me, cyclopentanone substituent) | 24 | D |
| (structure with SO₂Me, difluorocyclopentyl substituent) | 25 | D + N |

INHIBITION OF CYCLOOXYGENASE ACTIVITY

Compounds are tested as inhibitors of cyclooxygenase activity in whole cell cyclooxygenase assays. These assays measure prostaglandin $E_2$ synthesis in response to arachidonic acid, using a radioimmunoassay. Cells used for these assays are chinese hamster ovary (CHO) cell lines which have been stably transfected with an eukaryotic expression vector PCDNAIII containing either the human Cox-1 or Cox-2 CDNA's. U937 cell microsomes are also used to measure Cox-1 activity.

Whole Cell Assays for COX-2 and COX-1 Using CHO Transfected Cell Lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-2] cells prepared by trypsinization of adherent cultures are harvested by centrifugation (300×g, 10 min) and washed once in HBSS containing 15 mM HEPES, pH 7.4, and resuspended in HBSS, 15 mM HEPES, pH 7.4, at a cell concentration of 1.5×10⁶ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells (0.3×10⁶ cells in 200 μl) are preincubated with 3 μl of the test drug or DMSO vehicle for 15 min at 37° C. Working solutions of peroxide-free AA (5.5 μM and 110 μM AA for the CHO [hCOX-1] and CHO [COX-2] assays, respectively) are prepared by a 10-fold dilution of a concentrated AA solution in ethanol into HBSS containing 15 mM HEPES, pH 7.4.

Assay of COX-1 Activity from U937 Cell Microsomes

U 937 cells (ATCC CRL 1593) were cultured in 89% RPMI-1640 (SIGMA), 10% fetal bovine serum (GIBCO), containing 50 IU/ml penicillin (Flow labs), 50 mg/ml streptomycin (FLOW LABS) and 2 g/l NaHCO₃ (SIGMA). Cells were maintained at a density of 0.1–2.0×10⁶/ml in 1 liter spinner flasks (Corning) at 37∞C., 6% CO₂. For routine subculturing, cells were diluted in fresh medium and transferred to fresh flasks. U 937 cells are pelleted by centrifugation at 500×g for 5 min and washed once with phosphate-buffered saline and repelleted. Cells are resuspended in homogenization buffer consisting of 0.1 M Tris-HCl, pH 7.4, 10 mM EDTA, 2 μg/ml leupeptin, 2 μg/ml soybean trypsin inhibitor, 2 μg/ml aprotinin and 1 mM phenyl methyl sulfonyl fluoride. The cell suspension is sonicated 4 times for 10 sec and is centrifuged at 10,000×g for 10 min at 40° C. The supernatant is centrifuged at 100,000×g for 1 hr at 4° C. The 100,000×g microsomal pellet is resuspended in 0.1 M Tris-HCl, pH 7.4, 10 mM EDTA to approximately 7 mg protein/ml and stored at −80° C.

Microsomal preparations are thawed immediately prior to use, subjected to a brief sonication, and then diluted to a protein concentration of 125 μg/ml in 0.1 M Tris-HCl buffer, pH 7.4 containing 10 mM EDTA, 0.5 mM phenol, 1 mM reduced glutathione and 1 μM hematin. Assays are performed in duplicate in a final volume of 250 μl. Initially, 5 μl of DMSO vehicle or drug in DMSO are added to 20 μl of 0.1 M Tris-HCl buffer, pH 7.4 containing 10 mM EDTA in wells of a 96-deepwell polypropylene titre plate. 200 μl of the microsomal preparation are then added and pre-incubated for 15 min at room temperature before addition of 25 μl of 1 M arachidonic acid in 0.1 M Tris-HCl and 10 mM EDTA, pH 7.4. Samples are incubated for 40 min at room temperature and the reaction is stopped by the addition of 25 μl of 1 N HCl. Samples are neutralized with 25 μl of 1 N NaOH prior to quantitation of $PGE_2$ content by radioimmunoassay (Dupont-NEN or Amersham assay kits). Cyclooxygenase activity is defined as the difference between $PGE_2$ levels in samples incubated in the presence of arachidonic acid and ethanol vehicle.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_2$ production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2 mL blood aliquot to use as blank (basal levels of $PGE_2$). The remaining blood is incubated with LPS (100 μg/ml final concentration, Sigma Chem, #L-2630 from *E. coli*; diluted in 0.1% BSA (Phosphate buffered saline) for 5 minutes at room temperature. Five hundred μL aliquots of blood are incubated with either 2 μL of vehicle (DMSO) or 2 μL of a test compound at final concentrations varying from 10 nM to 30 μM for 24 hours at 37° C. At the end of the incubation, the blood is centrifuged at 12,000×g for 5 minutes to obtain plasma. A 100 μL aliquot of plasma is mixed with 400 μL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX-1 (Clotting-induced $TxB_2$ production)

Fresh blood is collected into vacutainers containing no anticoagulants. Aliquots of 500 μL are immediately transferred to siliconized microcentrifuge tubes preloaded with 2 μL of either DMSO or a test compound at final concentrations varying from 10 nM to 30 μM. The tubes are vortexed and incubated at 37° C. for 1 hour to allow blood to clot. At the end of incubation, serum is obtained by centrifugation (12,000×g for 5 min.). A 100 μL aliquot of serum is mixed with 400 μL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Protocol

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 ml of 1% carrageenan solution in saline (FMC Corp, Maine) into the paw using an insulin syringe with a 25-gauge needle (i.e. 500 mg carrageenan per paw). Three hr later, the paw volume ($V_3$) is measured and the increases in paw volume ($V_3-V_0$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-INDUCED GASTROPATHY IN RATS

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 Ci of sodium $^{51}$chromate for 30 min. at 37° C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 Ci) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ (5 Ci/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h and 8 h after the last drug dose, and plasma concentrations of drug measured by RP-HPLC.

LPS-Induced Pyrexia in Conscious Rats

Male Sprague-Dawley rats (150–200 g) were fasted for 16–18 h before use. At approximately 9:30 a.m., the animals were placed temporarily in plexiglass restrainers and their baseline rectal temperature was recorded using a flexible temperature probe (YSI series 400) connected to a digital thermometer (Model 08502, Cole Parmer). The same probe and thermometer were used for all animals to reduce experimental error. The animals were returned to their cages after the temperature measurements. At time zero, the rats were injected intraperitoneally with either saline or LPS (lipopoly-saccharide, 2 mg/kg, Sigma Chem) and the rectal temperature was remeasured at 5, 6 and 7 h following LPS injection. After the measurement at 5 h, when the increase in temperature had reached a plateau, the LPS-injected rats were given either the vehicle (1% methocel) or a test compound orally to determine whether the compound could reverse the pyrexia. Percent reversal of the pyrexia was calculated using the rectal temperature obtained at 7 h in the control (vehicle-treated) group as the reference (zero reversal) point. Complete reversal of pyrexia to the pre-LPS baseline value is taken as 100%.

LPS-Induced Pyrexia in Conscious Squirrel Monkeys

Temperature probes were surgically implanted under the abdominal skin in a group of squirrel monkeys (Saimiri sciureus) (1.0–1.7 kg). This allows for the monitoring of body temperature in conscious, unrestrained monkeys by a telemetric sensing system (Data Sciences International, Minnesota). The animals were fasted and were placed in individual cages for acclimatization 13–14 h before use. Electronic receivers were installed on the side of the cages which pick up signals from the implanted temperature probes. At approximately 9:00 a.m. on the day of the experiment, the monkeys were restrained temporarily in training chairs and were given a bolus I.V. injection of LPS, (6 mg/kg, dissolved in sterile saline). The animals were returned to their cages and body temperature was recorded continuously every 5 min. Two h after injection of LPS, when the body temperature had increased by 1.5–2∞C., the monkeys were dosed orally with either vehicle (1% methocel) or a test compound (3 mg/kg). One hundred minutes later, the difference between the body temperature and the baseline value was determined. Percent inhibition was calculated taking the value in the control group as 0% inhibition.

Acute Inflammatory Hyperalgesia Induced by Carrageenan in Rats

Experiments were performed using male Sprague Dawley rats (90–110 g). Hyperalgesia to mechanical compression of the hind paw was induced by intraplantar injection of carrageenan (4.5 mg into one hind paw) 3 h previously. Control animals received an equivalent volume of saline (0.15 ml intraplantar). A test compound (0.3–30 mg/kg, suspended in 0.5% methocel in distilled water) or vehicle (0.5% methocel) was administered orally (2 ml/kg) 2 h after carrageenan. The vocalisation response to compression of the hind paw was measured 1 h later using a Ugo Basile algesiometer.

Statistical analysis for carrageenan-induced hyperalgesia was performed using one-way ANOVA (BMDP Statistical Software Inc.). Hyperalgesia was determined by subtracting the vocalisation threshold in saline injected rats from that obtained in animals injected with carrageenan. Hyperalgesia scores for drug-treated rats were expressed as a percentage of this response. $ID_{50}$ values (the dose producing 50% of the maximum observed response) were then calculated by non-linear least squares regression analysis of mean data using GraFit (Erithacus Software).

Adjuvant-Induced Arthritis in Rats

Seventy, 6.5–7.5 week old, female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium butyricum* in 0.1 ml of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day-1) and 21 days following adjuvant injection, and primary paw volumes were determined before (day-1) and on days 4 and 21 following adjuvant injection. The rats were anesthetized with an intramuscular injection of 0.03–0.1 ml of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subchondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, Indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

Two-factor ('treatment' and 'time') analysis of variance with repeated measures on 'time' were applied to the % changes for body weight and foot volumes and to the rank-transformed radiographic total scores. A post hoc Dunnett's test was conducted to compare the effect of treatments to vehicle. A one-way analysis of variance was applied to the thymic and spleen weights followed by the Dunnett's test to compare the effect of treatments to vehicle. Dose-response curves for % inhibition in foot volumes on days 4, 14 and 21 were fitted by a 4-parameter logistic function using a non-linear least squares' regression. $ID_{50}$ was defined as the dose corresponding to a 50% reduction from the vehicle and was derived by interpolation from the fitted 4-parameter equation.

Representative Biological Data

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control.

The results for certain of the biological assays may be seen Tables II and III.

TABLE II

| Example | Rat Paw Edema $ED_{50}$ (mg/kg) |
|---|---|
| 2 | 1.0 |
| 3 | 2.4 |
| 8 | 3.1 |
| 10 | 3.2 |
| 11 | 2.3 |
| 17 | 0.9 |
| 23 | 5.9 |

TABLE III

| | COX-2 (IC50) | | COX-1 (IC50) | | |
|---|---|---|---|---|---|
| Example | CHO uM | HWB uM | U937 uM | CHO uM | HWB uM |
| 1 | 0.05 | 1.9 | | | |
| 2 | 0.04 | <0.4 | | | |
| 3 | 0.1 | <0.4 | | | |
| 4 | 0.6 | 0.9 | | | |
| 5 | 0.08 | 0.6 | | | |
| 6 | 0.01 | 0.08 | | | |
| 7 | 0.07 | 2.1 | | | |
| 8 | 0.5 | 0.5 | | | |
| 9 | 0.4 | <0.4 | | | |
| 10 | 0.05 | 0.14 | | 100 | |
| 11 | 0.09 | 0.08 | | >50 | |
| 12 | 0.5 | 4.7 | | | |

TABLE III-continued

| | COX-2 (IC50) | | COX-1 (IC50) | | |
|---|---|---|---|---|---|
| Example | CHO uM | HWB uM | U937 uM | CHO uM | HWB uM |
| 13 | 0.1 | 0.6 | | | |
| 14 | 0.5 | 5.1 | | | |
| 15 | 0.2 | 1.8 | | | |
| 16 | 0.4 | | | | |
| 17 | 0.3 | 0.6 | | | |
| 18 | | <0.4 | | | |
| 19 | | <0.4 | | | |
| 20 | 0.2 | 0.6 | | | |
| 21 | 0.6 | 0.9 | | | |
| 22 | 0.1 | <0.4 | | | |
| 23 | 0.1 | <0.4 | | | |
| 24 | 0.4 | 0.8 | | | |
| 25 | | <0.4 | | | |

The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), M.P. (melting point), L (liter(s)), mL (milliliters), g (gram (s)), mg (milligrams(s)), mol (moles), mmol (millimoles), eq (equivalent(s)).

EXAMPLE 1

5,5-Dimethyl-3-((1-methylallyl)oxy)-4-(4-methylsulfonylphenyl)-5H-furan-2-one

Step 1: 2-Methyl-1-(4-(methylthio)phenyl)-propan-1-one

To a suspension of aluminum chloride (136 g, 1.02 mol) in chloroform (1.0 L) cooled to −10° C., was added dropwise isobutyrylchloride (115 mL, 1.10 mol). Then thioanisole (100 mL, 0.85 mol) was added dropwise. Upon completion of addition the reaction was allowed to proceed at r.t. for 1.5 h. The reaction was cooled to 10° C. and quenched by addition of water (750 mL). The organic layer was separated, washed with water (2×500 mL), saturated $NaHCO_3$ solution(2×500 mL), brine (1×500 mL), and then dried over $Na_2SO_4$. After concentration in vacuo., the resulting crude product crystallized upon standing under high vacuum for 30 min to give the title compound as a brown solid.

Step 2: 2-Hydroxy-2-methyl-1-(4-(methylthio)phenyl) propan-1-one

To a solution of 2-methyl-1-(4-(methylthio)phenyl) propan-1-one (28.5 g, 147 mmol, Step 1), Aliquat 336 (11.0 mL, 24 mmol) and carbon tetrachloride (21 mL, 218 mmol) in toluene (43 mL) was added sodium hydroxide (12.9 g, pellets, 322 mmol). The reaction was stirred at 15° C. for 2 h and then at r.t. for 16 h. The reaction was diluted with water (100 mL), brine (100 mL) and EtOAc (300 mL). The aqueous phase was acidified with 1 N HCl and extracted with EtOAc (100 mL). The combined organic layers were dried over $Na_2SO_4$ and concentrated. The crude product was purified by silica gel chromatography eluted with 15% EtOAc in hexane to give the title compound as a thick syrup.

Step 3: 2-Hydroxy-2-methyl-1-(4-(methylsulfonyl)phenyl) propan-1-one

To a cold (4° C.) solution of 2-hydroxy-2-methyl-1-(4-(methylthio)phenyl)propan-1-one (45.0 g, 214 mmol, Step 2) in t-butanol (500 mL) and $CH_2Cl_2$ (500 mL) was added a solution of OXONE™ (194 g, 316 mmol) in water (1.4 L). The resulting suspension was stirred at r.t. for 18 h. The reaction was diluted with EtOAc (400 mL) and the layers were separated. The aqueous layer was extracted with EtOAc (2×250 mL). The combined organic layers were dried over $Na_2SO_4$ and concentrated in vacuo. The crude product was dissolved in diethyl ether (250 mL), hexane was added (150 mL) and the product was swished for 2 h. The product was collected by filtration to give the title compound as a yellow solid.

Step 4: (1-Methylallyloxy) acetic acid

To a solution of 1-buten-3-ol (25 mL, 288 mmol) in THF (250 mL) at 0∞C. was added NaH (8.6 g, 288 mmol, 80% in oil). After the NaH had been consumed, bromoacetic acid (10 g, 71.9 mmol) was added. The reaction was then allowed to stir at r.t. overnight. The mixture was then cooled to 0∞C., and ice was added followed by cold 6 M HCl (75 mL). The product was extracted with EtOAc and the organic layer was washed with $H_2O$ and brine. After drying ($MgSO_4$), filtration, and removal of the solvent, beige coloured oil (10.5 g) was obtained. This was used without further purification.

Step 5: (1-Methylallyloxy)acetic acid 2-methyl-1-(4-methylsulfonylphenyl)propan-1-one-2yl ester To a solution of the alcohol of Step 3 (2.87 g, 11.8 mmol) and the acid from step 1 (2.0 g, 15.4 mmol) in $CH_2Cl_2$ (30 mL) was added CMC (7.5 g, 17.7 mmol), along with 50 mg of DMAP. After stirring overnight, $H_2O$ (20 mL) was ad ded and the product was extracted with $CH_2Cl_2$. The organic layer was dried ($MgSO_4$), filtered and evaporated. Purification was effected by flash chromatography (1:5 EtOAc:hexane) to yield 2.97 g of an oil.

Step 6: 5,5-Dimethyl-3-(1-methylallyl)oxy)-4-(4-methylsulfonyl) phenyl)-5H-furan-2-one To a solution of the ester from Step 5, (2.97 g, 8.3 mmol) in $CH_3CN$ (30 mL) was added DBU (1.87 mL, 12.6 mmol) and isopropyl trifluoroacetate (1.53 mL, 10.9 mmol). The mixture was stirred at 65∞C. for 20 h. $H_2O$ (60 mL) was then added, followed by 6M HCl until the dark colour faded. The product was extracted with EtOAc and the organic layer was washed with $H_2O$ and brine. After drying ($MgSO_4$) and filtration through a plug of silica gel, the solvent was removed to give a pale brown residue. Purification was effected by flash chromatography (1:5 EtOAc: hexane) to give an off white solid. This was recrystallized from EtOAc:hexane to give a white solid (228 mg).

$^1$H NMR d 1.34–1.39 (3H, m), 1.65 (6H, s), 3.18 (3H, s), 5.11–5.17 (1H, m) 5.17–5.25 (1H, m), 5.43–5.53 (1H, m), 5.77–5.89 (1H, m), 7.98–8.08 (4H, m).

EXAMPLE 2

5,5-Dimethyl-3-(1,1,1,3,3,3-hexafluoropropoxy)-4-(4-methylsulfonyl-phenyl)-5H-furan-2-one Step 1,1,1,3,3,3-Hexafluoropropoxyacetic acid The title compound was prepared as described in Example 1 Step 4 using 1,1,1,3,3,3-hexafluoro-2-propanol.

Step 2 2-methyl-1-(4-methylthiophenyl)propan-1-one-2yl ester

The title compound was prepared as described in Example 1 Step 5, using the tertiary alcohol of Example 1 Step 2.

Step 3 5,5-Dimethyl-3-(1,1,1,3,3,3-hexafluoropropoxy)-4-(4-methylthiophenyl)-5H-furan-2-one The title compound was prepared using conditions described in Example 1 Step 6 except that isopropyltrifluoroacetate was not added to the reaction mixture.

Step 4 5,5-Dimethyl-3-(1,1,1,3,3,3-hexafluoropropoxy)-4-(4-methylsulfonylphenyl)-5H-furan-2-one The title compound was prepared using conditions described in Example 1 Step 3, except that MeOH was used instead of t-butanol.

$^1$H NMR (CD$_3$COCD$_3$) d 1.70 (6H, s), 3.20 (3H, s), 6.47 (1H, m), 8.00 (4H, dd).

EXAMPLE 3

5,5-Dimethyl-3-((1-methyl-2-propynyl)oxy)-4-(4-methylsulfonylphenyl)-5H-furan-2-one Step 1 (1-methyl-2-propynyloxy)acetic acid The title compound was prepared as described in Example 1 Step 4 except the reaction mixture was refluxed overnight.

Step 2 (1-methyl-2-propynyloxy)acetic acid 2-methyl-1-(4-methylsulfonylphenyl)propan-1-one-2yl ester The title compound was prepared as described in Example 1 Step 5.

Step 3 5,5-Dimethyl-3-((1-methyl-2-propynyl)oxy)-4-(4-methylsulfonylphenyl)-5H-furan-2-one The title compound was prepared using conditions described in Example 1 Step 6 except that the reaction was performed with 4 equivalents of DBU and without isopropyl trifluoroacetate.

$^1$H NMR (CD$_3$COCD$_3$) d 1.55 (3H, d), 1.70 (6H, 2s), 3.20 (3H, s), 5.80 (1H, m), 8.00 (4H, m).

EXAMPLE 4

3-((1R, 2S)-(1S, 2R)-2-hydroxy-1-methylpropyl)oxy)-5,5-dimethyl-4-(4-methylsulfonylphenyl)-5H-furan-2-one Step 1 5,5-Dimethyl-3-hydroxy-4-(4-methylsulfonylphenyl)-5H-furan-2-one To a 0° C. solution of the alcohol of Example 1, Step 3 (29.5 g, 122 mmol) in CH$_3$CN (350 mL) were added pyridine (25 mL) and acetoxyacetyl chloride (25 g, 183 mmol). After a period of 7 h at r.t., DBU (31 mL) was added to the reaction mixture. After a period of 1 h at 80° C., a second portion of DBU (35 mL) was added. The reaction mixture was kept at 80° C. for 18 h. The reaction mixture was allowed to cool to r.t. The mixture was poured onto ice-water (2.5 L) containing 100 mL of concentrated HCl. The brown solid was collected and dissolved in hot acetonitrile and was filtered through a plug of silica. The solvent was evaporated and the resultant solid was swished in EtOAc to give the title compound (21.2 g, 62%).

Step 2 3-((1R, 2S)-(1S, 2R)-2-hydroxy-1-methylpropyl)oxy)-5,5-dimethyl-4-(4-methylsulfonylphenyl)-5H-furan-2-one A sealed tube was charged with the hydroxy lactone of Step 1 (300 mg, 1.06 mmol) in 1.06 mL EtOH, trans-2,3-epoxybutane (307 mg, 4.25 mmol) and Et$_3$N (430 mg, 4.25 mmol). The mixture was heated at reflux for 48 h. After cooling the mixture was poured into 5% aq HCl (10 mL) and extracted with EtOAc (3×20 mL). The combined organic layers were washed with brine (1×30 mL) and dried over MgSO$_4$. Flash chromatography (40% EtOAc in toluene) gave 34 mg of product; mp. 121–122∞C., MS m/z 355 (M+H)$^+$.

EXAMPLE 5

3-((2-hydroxy-2-methyl-3-butenyl)oxy)-5,5-dimethyl-4-(4-methyl-sulfonyl)phenyl-5H-furan-2-one To a solution of the hydroxy lactone of Example 4 Step 1, (500 mg, 1.77 mmol) in 1.4 ml EtOH was added Et$_3$N (717 mg, 7.08 mmol) and 2-methyl-2-vinyloxirane (596 mg, 7.08 mmol). The mixture was stirred at 50° C.; for 16 h the solvent was evaporated and the residue was chromatographed on silica gel (40% EtOAc in toluene). The product was further purified by stirring in Et$_2$O/hexane. The product was filtered to give 20 mg of an off white solid. MS m/z 367 (M+H)$^+$.

EXAMPLE 6

3-(2-Bromo-1-methylethoxy)-5,5-dimethyl-4-(4-methylsulfonylphenyl)-5H-furan-2-one To a suspension of the alcohol of Example 4 Step 1, (1.00 g, 3.59 mmol) in benzene (40.0 mL) were added an excess of 1,2-dibromo propane (0.50 mL) and Ag$_2$CO$_3$ (3.00 g, 10.8 mmol). After a period of 18 h at 60∞C., the reaction mixture was filtered over celite and washed with CH$_2$Cl$_2$. After evaporation, the crude product was purified by flash chromatography to provide 162 mg of the title compound after crystallization with Et$_2$O/hexane.

$^1$H NMR (CD$_3$COCD$_3$) d 1.40 (3H, d), 1.65 (6H, 2s), 3.20 (3H, s), 3.70 (2H, m), 5.40 (1H, m), 8.05 (4H, m).

EXAMPLE 7

3-(Isopropenyloxy)-5,5-dimethyl-4-(4-methylsulfonylphenyl)-5H-furan-2-one

To the bromide of Example 6 (300 mg, 0.746 mmol) in THF (10 mL) was added 1.5 mL of a 1M THF solution of potassium tert-butoxide. The resulting mixture was stirred at room temperature for 1 h. The reaction mixture was then partitioned between 25% NH$_4$OAc and EtOAc. The organic phase was dried over Na$_2$SO$_4$, filtered and evaporated. After flash chromatography, 100 mg of the title compound was obtained.

$^1$H NMR (CD$_3$COCD$_3$) d 1.70 (6H, s), 1.90 (3H, s), 3.20 (3H, s), 4.10 and 4.20 (2H, m), 8.00 (4H, m).

EXAMPLE 8

3-(((2S)-3-hydroxy-2-methylpropyl)oxy)-5,5-dimethyl-4(4-methyl-sulfonylphenyl)-5H-furan-2-one Step 1 (2S)-1-Bromo-3-(t-butyldiphenylsilyloxy)-2-methylpropane To a solution of (S)-(+)-3-bromo-2-methyl-1-propanol (780 mg, 5.16 mmol) in $CH_2Cl_2$ (13 mL) were added $Et_3N$ (1.07 mL, 7.69 mmol), tert-butylchlorodiphenylsilane (1.70 g, 6.18 mmol) and DMAP (30 mg). After a period of 3 h at room temperature, 25% aqueous $NH_4OAc$ was added and the organic phase was separated, dried over $Na_2SO_4$ and evaporated. The title compound was purified by flash chromatography to provide 1.8 g of an oil.

Step 2 3-(((2R)-3-t-butyldiphenylsilyloxy)-2-methylpropyl)oxy)-5,5-dimethyl-4-(4-methylsulfonylphenyl)-5H-furan-2-one To the alcohol of Example 4 Step 1 (629 mg, 2.23 mmol) in DMF (6.3 mL) were added the bromide of Step 1 (1.30 g, 3.34 mmol), $nBu_4NI$ (822 mg, 2.23 mmol) and NaH 60% in oil (126 mg, 3.15 mmol). After a period of 5 h at 70∞C., the reaction mixture was partitioned between 25% $NH_4OAc$ and EtOAc. The organic phase was separated, dried over $Na_2SO_4$, filtered and evaporated under reduced pressure. The title compound was purified by flash chromatography to give 1.5 g of material.

Step 3 3-(((2S)-3-hydroxy-2-methylpropyl)oxy)-5,5-dimethyl-4(4-methylsulfonylphenyl)-5H-furan-2-one To the silyl ether of Step 2 (1.6 g, 2.70 mmol) in THF (14 mL) was added a 1M THF solution of tetrabutylammonium fluoride (4.05 mL, 4.05 mmol). After a period of 1.5 h at room temperature, the reaction was partitioned between 25% aqueous $NH_4OAc$ and EtOAc. The organic phase was separated, dried over $Na_2SO_4$, filtered and evaporated. The title compound (800 mg) was obtained after purification by flash chromatography.

$^1$H NMR ($CD_3COCD_3$) d 0.90 (3H, d), 1.60 (6H, s), 1.90 (1H, m), 3.20 (3H, s), 3.50 (2H, t), 3.60 (1H, t), 4.20 and 4.40 (2H, m), 8.00 (4H, m).

EXAMPLE 9

3-(((2R)-3-hydroxy-2-methylpropyl)oxy)-5,5-dimethyl-4-(4-methylsulfonylphenyl)-5H-furan-2-one To the alcohol of Example 4, Step 1 (3.00 g, 10.6 mmol) in DMF (35 mL) were added (R)-(−)-3-bromo-2-methyl-1-propanol (3.00 g, 19.6 mmol), $nBu_4NI$ (3.00 g, 8.10 mmol) and NaH 80% in oil (0.91 g, 30 mmol). After a period of 5 h at 70∞C., the reaction mixture was partitioned between 25% $NH_4OAc$ and EtOAc. The organic phase was separated, dried over $Na_2SO_4$, filtered and evaporated. The title compound (390 mg) was purified by flash chromatography.

$^1$H NMR ($CD_3COCD_3$) d 0.90 (3H, d), 1.60 (6H, s), 1.90 (1H, m), 3.20 (3H, s), 3.50 (2H, t), 3.60 (1H, t), 4.20 and 4.40 (2H, m), 8.00 (4H, m).

EXAMPLE 10

3-(((2R)-3-Fluoro-2-methylpropyl)oxy)-5,5-dimethyl-4-(4-methylsulfonylphenyl)-5H-furan-2-one To the alcohol of Example 8 Step 3 (800 mg, 2.25 mmol) in $CH_2Cl_2$ (10 mL) at −20∞C. were added $Et_3N$ (943 mL, 6.05 mmol) and MsCl (348 mL, 4.51 mmol). After a period of 1 h at 0∞C., saturated $NaHCO_3$ was added. The organic phase was separated, dried over $Na_2SO_4$, filtered and evaporated. To the crude mesylate in THF (10.0 mL) was added a 1M THF solution of tetrabutylammonium fluoride (6.77 mL, 6.77 mmol). After a period of 2 h at 50∞C., the reaction mixture was partitioned between 25% $NH_4OAc$ and EtOAc. The organic phase was separated, dried over $Na_2SO_4$, filtered and evaporated. The title compound (370 mg) was purified by flash chromatography.

$^1$H NMR ($CD_3COCD_3$) d 0.90 (3H,d), 1.60 (6H, s), 2.20 (1H, m), 3.20 (3H, s), 4.20 to 4.50 (4H, m), 8.00 (4H, m).

EXAMPLE 11

3-(((2S)-3-fluoro-2-methylpropyl)oxy)-5,5-dimethyl-4-(4-methylsulfonylphenyl)-5H-furan-2-one The title compound was prepared from the alcohol of Example 9 as described in Example 10.

$^1$H NMR($CD_3COCD_3$) d 0.90 (3H, d), 1.60 (6H, s), 2.20 (1H, m), 3.20 (3H, s), 4.20 to 4.50 (4H, m), 8.00 (4H, m).

EXAMPLE 12

3-(2-Hydroxy-1-methylethoxy)-5,5-dimethyl-4-(4-methylsulfonyl-phenyl)-5H-furan-2-one Step 1: Methyl 2-((5,5-dimethyl-4-(4-methylsulfonylphenyl)-2-oxo-2,5-dihydro-3-furanyl)oxy)propanoate The title compound was prepared as described in Example 8 except the reaction was performed at room temperature.

Step 2 3-(2-Hydroxy-1-methylethoxy)-5,5-dimethyl-4-(4-methylsulfonylphenyl)-5H-furan-2-one To the ester of Step 1 (1.13 g, 3.07 mmol) in $CH_2Cl_2$ (30 mL) and $Et_2O$ 50 mL was added at 0∞C. $LiBH_4$ (80 mg, 3.68 mmol). The reaction mixture was stirred at room temperature until completion. The reaction mixture was partitioned between 25% $NH_4OAc$ and EtOAc. The organic phase was separated, dried over $Na_2SO_4$ and evaporated. The title compound (275 mg) was obtained as a white solid after purification by flash chromatography.

$^1$H NMR ($CD_3COCD_3$) d 1.20 (3H, d), 1.80 and 1.65 (6H, 2s), 3.20 (3H, s), 3.60 (2H, m), 3.95 (1H, t), 5.10 (1H, m), 8.00 (4H, m).

EXAMPLE 13

3-(2-Fluoro-1-methylethoxy)-5,5-dimethyl-4-(4-methylsulfonylphenyl)-5H-furan-2-one To the alcohol of Example 12 Step 2 (300 mg, 0.882 mmol) in $CH_2Cl_2$ (10 mL) at 0∞C. was added DAST (142 mL, 1.05 mmol). After a period of 18 h at room temperature and 2 days at reflux, the reaction mixture was partitioned between 25% aqueous $NH_4OAc$ and EtOAc. The organic phase was separated, dried over $Na_2SO_4$, filtered and evaporated under reduced pressure. The title compound (48 mg) was purified by flash chromatography.

$^1$H NMR ($CD_3COCD_3$) d 1.30 (3H, d), 1.70 (6H, 2s), 4.30–4.70 (2H, m), 5.35 (1H, m), 8.00 (4H, m).

EXAMPLE 14

5,5-Dimethyl-4-(4-methylsulfonylphenyl)3-(2-propynyloxy)-5H-furan-2-one

The title compound was prepared as described in Example 8, Step 2.

$^1$H NMR($CD_3COCD_3$) d 1.60 (6H, s), 3.15 (1H, m), 3.20 (3H, s), 5.00 (2H, m), 8.00 (4H, m).

EXAMPLE 15

3-(Allyloxy)-5,5-dimethyl-4-(4-methylsulfonylphenyl)-5H-furan-2-one

The title compound was prepared as described in Example 8, Step 2.

¹H NMR (CD₃COCD₃) d 1.60 (6H, s), 3.20 (3H, s), 4.80 (2H, m), 5.30 (2H, m), 6.00 (1H, m), 8.00 (4H, m).

EXAMPLE 16

3-(1,4-dioxaspiro[4.5]dec-8-yloxy)-5,5-dimethyl-4-(4-methylsulfonyl-phenyl)-5H-furan-2-one Step 1: 1,4-dioxaspiro[4.5]decan-8-ol To an ice cold solution of 1,4-cyclohexadione mono-ethylene ketal (10.1 g, 65 mmol) in ethanol (180 mL) was added sodium borohydride (1.23 g, 32 mmol) and the resulting suspension was stirred at room temperature for 19 h. The reaction was diluted with 25% NH₄OAc aqueous solution and extract with EtOAc. The organic layer was dried over MgSO₄ and concentrated. Purification by silica gel chromatography (70% EtOAc/Hexane) provided 9.73 g of the title compound as a colorless oil.

Step 2: 1,4-dioxaspiro[4.5]dec-8-yl methanesulfonate

To an ice cold solution of the alcohol from Step 1 (4.59 g, 29 mmol) and triethylamine (8.0 mL, 57 mmol) in dichloromethane (100 mL) was added methanesulfonyl chloride (3.3 mL, 43 mmol). The reaction was then diluted with water (80 mL) and extracted with CH₂Cl₂ (2×50 mL). The combined organic layers were dried over MgSO₄ and concentrated to give the title compound as a yellow oil.

Step 3: 8-Iodo-1,4-dioxaspiro[4.5]decane and 4-Iodocyclohexanone

To a solution of mesylate from Step 2 (7.38 g) in acetone (100 mL) was added lithium iodide (20.2 g, 151 mmol). The resulting suspension was heated at 70∞C. for 1 hour. The reaction was allowed to cool to room temperature, it was diluted with EtOAc (200 mL) and washed with water (2×70 mL). The organic layer was dried over MgSO₄ and concentrated. Separation of the 2 title compounds was achieved by silica gel chromatography (25 and 35% Et₂O/hexane).

¹H NMR of 4-Iodocyclohexane (CD₃COCD₃) d 2.30 (4H, m), 2.41 (4H, m), 4.86 (1H, m).

Step 4: 3-(1,4-dioxaspiro[4.5]dec-8yloxy)-5,5-dimethyl-4-(4-methylsulfonylphenyl)-5H-furan-2-one Following the procedure described for Example 6 the title compound was prepared from 8-Iodo-1,4-dioxaspiro[4.5]decane (Step 3).

M.P. 133–134∞C. ¹H NMR (CD₃COCD₃) d 1.47 (2H, m), 1.67 (2H, m and 6H, s), 1.78 (2H, m), 1.96 (2H, m), 3.17 (3H, s), 3.87 (4H, s), 4.98 (1H, m), 7.99 (2H, d), 8.06 (2H, d).

EXAMPLE 17

3-[(4,4-difluorocyclohexyl)oxy]-5,5-dimethyl-4(4-(methylsulfonyl-phenyl)-5H-furan-2-one Step 1 5,5-dimethyl-4-[4-(methylsulfonyl)phenyl]-3-[(4-oxocyclohexyl)oxy]-5-H-furan-2

Following the procedure described for example 6 the title compound was prepared from 4-iodocyclohexanone (Example 16, Step 3).

Step 2

To an ice cold solution of the ketone from step 1 (419 mg, 1.1 mmol) in CH₂Cl₂ (0.5 mL) was added diethylaminosulfur trifluoride and the resulting mixture was heated at 60∞C. for 2 hours. The reaction was allowed to cool to room temperature and then carefully diluted with aqueous NaHCO₃ saturated. The mixture was extracted with EtOAc. The organic layer was dried over MgSO₄ and concentrated. Purification by silica gel chromatography (40% EtOAc/Hexane) followed by crystalization in EtOAc/Hexane (1:2, 30 mL) provided the title compound as a white solid.

M.P. 147–148∞C.;

¹H NMR (CD₃COCD₃) d 1.68 (6H, s), 1.80–1.97 (8H, m), 3.17 (3H, s), 5.04 (1H, bd), 7.98 (2H, d), 8.07 (2H, d).

EXAMPLE 18

5,5-dimethyl-3-(2-methylallyloxy)-4-(4-methylsulfonylphenyl)-5H-furan-2-one

To a solution of 3.6 g of the hydroxy lactone of Example 4 Step 1 in 50 mL DMF was added 2.5 mL of methylallyl bromide followed by 0.5 g of NaH (80% in mineral oil). The mixture was stirred for 6 h at room temperature and then quenched with 50 mL of saturated solution of NH₄Cl. The product was extracted with 2:1 EtOAc/hexane (200 mL) and the extract was dried over MgSO₄. After filtration and concentration, the residue was purified by flash chromatography eluted with 2:1 hexane/EtOAc to give 3.7 g of the title compound as a white solid.

¹H NMR (CD₃COCD₃) d 1.64 (6H, s), 1.67 (3H, s), 3.17 (3H, s), 4.74 (2H, s), 4.92 (1H, s), 4.96 (1H, s), 7.96 (2H, d), 8.06 (2H, d).

EXAMPLE 19

5,5-Dimethyl-3-[(1-methylcyclopropyl)methoxy]-4-(4-methylsulfonyl-phenyl)-5H-furan-2-one To a solution of Et₂Zn (0.82 mL) in 50 mL of ClCH₂CH₂Cl cooled at 0∞C. was added 1.3 mL of CH₂I₂ slowly. The mixture was stirred for 5 min. and treated with 0.63 g of the olefin of example 18 at 0∞C. The mixture was stirred for 20 min. at 0∞C. and 3 h at room temperature. The reaction was quenched by addition of 50 mL of saturated NH₄Cl solution and the product was extracted with EtOAc (200 mL) The extract was dried over MgSO₄, filtered and concentrated. The crude product was purified by flash chromotography eluted with 3:2 hexane/EtOAc to give 400 mg of the title product as a white solid.

¹H NMR (CD₃COCD₃) d 0.35 (2H, m), 0.49 (2H, m), 1.10 (3H, s), 1.65 (6H, s), 3.15 (3H, s), 4.13 (2H, s), 8.05 (4H, m).

EXAMPLE 20

3-{[2-(fluoromethyl)allyl]oxy}-5,5-dimethyl-4-(4-methylsulfonyl-phenyl)-5H-furan-2-one Step 1 3-{[2-(chloromethyl)allyl]oxy}-5,5-dimethyl-4-(4-methylsulfonylphenyl)-5H-furan-2-one To a solution of 1.2 g of the hydroxy lactone of Example 4 Step 1 in 20 mL of DMF was added 0.24 g of NaH (60% in mineral oil) followed by 4 mL of 3-chloro-2-chloromethyl-1-propene. The mixture was stirred for 14 h at room temperature and then quenched with 50 mL of saturated solution of NH₄Cl. The mixture was extracted with 100 mL of 1:1 hexane/EtOAc and the extract was dried over MgSO₄. After filtration and concentration the crude product was purified by flash chromatography eluted with 1:1 hexane/EtOAc to give 1 g of the title compound as a thick oil.

Step 2 3-{[2-(hydroxymethyl)allyl]oxy}-5,5-dimethyl-4-(4-methylsulfonylphenyl)-5H-furan-2-one A solution of the product of Step 1 (1.0 g) 3g of Bu₄NOAc and 10 mg of Bu₄NI in 25 mL of CH₃CN was stirred for 4 h at room temperature. The solvent was then removed by evaporation and the residue was partitioned between 40 mL brine and 100 mL EtOAc. The EtOAc layer was concentrated and the residue was dissolved in 40 mL of 1:1 THF/H₂O and treated with 10 mL of 1N LiOH. After stirring for 20 min. at room temperature, the mixture was treated with 1 mL AcOH and then partioned between 50 mL brine and 100 mL EtOAc. The organic layer was dried over MgSO$_4$ and concentrated to give the crude title compound as an oil which was used for the next step without further purification.

Step 3 3-{[2-(fluoromethyl)allyl]oxy}-5,5-dimethyl-4-(4-methylsulfonylphenyl)-5H-furan-2-one To a solution of the crude product of Step 2 in 20 mL of CH$_2$Cl$_2$ was added 3 mL of diethylaminosulfuir trifluoride. The mixture was heated to reflux for 30 min. and then poured into 50 mL of saturated solution of NaHCO$_3$. The product was extracted with 100 mL of 1:1 EtOAc/hexane. The extract was dried over MgSO$_4$, filtered and concentrated. The residue was purified by flash chromatography eluted with 4:1 toluene/EtOAc to give 0.6 g of the title compound as a white solid.

$^1$H NMR(CD$_3$COCD$_3$) d 1.65 (6H, s), 3.17 (3H, s), 4.87 (2H, d), 4.91 (2H, s), 5.34 (1H, b), 5.36 (1H, bs), 7.93 (2H, d), 8.06 (2H, d).

EXAMPLE 21

3-{[1-(hydroxymethyl)cyclopropyl]methoxy}-5,5-dimethyl-4-(4-methylsulfonylphenyl)-2-5H-furan-2-one To a solution of 5 g of the hydroxy lactone of Example 4 Step 1 in 100 mL of DMF was added 1 g of NaH (60% in mineral oil), followed by 3 g of 5,7-dioxa-6l$^6$-thiaspiro[2.5] octane-6,6-dioxide. The mixture was stirred for 16 h at room temperature and then treated with 2 mL MeOH and 1 mL of AcOH. The solvent was removed under reduced pressure and the residue was dissolved in 150 mL of 1,4-dioxane. The solution was treated with 1.5 mL concentrated H$_2$SO$_4$. After stirring for 15 h at room temperature, 5 mL Et$_3$N was added and the mixture was concentrated. The residue was purified by flash chromatography eluted with 2:3 toluene/EtOAc to give 2.9 g of the title compound as a white solid.

$^1$H NMR(CD$_3$COCD$_3$) d 0.51 (4H, bs), 1.66 (6H, s), 3.17 (3H, s), 3.44 (2H, d), 3.65 (1H, t), 4.29 (2H, s), 8.04 (4H, s).

EXAMPLE 22

3-[(1-fluorocyclobutyl)methoxy]-5,5-dimethyl-4-(4-methylsulfonylphenyl)-5H-furan-2-one To a solution of 0.6 g of the product of Example 21 in 5 mL of CH$_2$Cl$_2$ was treated with 1.25 mL of diethylaminosulfur trifluoride at 0∞C. After stirring for 3 h at room temperature, the reaction mixture was poured into saturated solution of NaHCO$_3$ and extracted with EtOAc (50 mL). The extract was dried over MgSO$_4$ and concentrated. The crude product was purified by flash chromatography eluted with 2:1 hexane/EtOAc to give 400 mg of the title product as a white solid.

$^1$H NMR (CD$_3$COCD$_3$) d 1.14–1.52 (1H, m), 1.67 (6H, s), 1.65–1.80 (1H, m), 2.20–2.32 (4H, m), 3.17 (3H, s), 4.57 (2H, s), 8.02 (4H, m).

EXAMPLE 23

3-{[1-(fluoromethyl)cyclopropyl]methoxy}-5,5-dimethyl-4-(4-methylsulfonylphenyl)-5H-furan-2-one A solution of 0.2 g of the product of Example 21 and 0.4 mL of Et$_3$N in 5 mL of CH$_2$Cl$_2$ was cooled at −40∞C. and treated with 0.13 mL of methanesulfonyl chloride. After stirring for 10 min. at −40∞C., the reaction was quenched with 10 mL of saturated solution NaHCO$_3$ and extracted with 25 mL of EtOAc. The extract was dried over MgSO$_4$ and concentrated to give the crude mesylate as an oil. The crude mesylate was dissolved in 15 mL of THF and treated with 3 mL of 1M nBu$_4$NF in THF. After stirring at 50∞C. for 1 h, the reaction mixture was poured into 50 mL of brine and extracted with 50 mL of EtOAc. The extract was dried over MgSO$_4$, filtered and concentrated. The crude product was purified by flash chromatography eluted with 1:1 hexane/EtOAc to give 0.13 g of the title compound as a white solid.

$^1$H NMR(CD$_3$COCD$_3$) d 0.67 (4H, m), 1.65 (6H, s), 3.17 (3H, sZ), 4.28 (2H, d), 4.28 (2H, s), 8.02 (2H, d), 8.06 (2H, d).

EXAMPLE 24

3-((2-oxocyclopentyl)oxy)-5,5-dimethyl-4-(4-methylsulfonylphenyl)-5H-furan-2-one A solution of the hydroxylactone of Example 4 Step 1 (2.19 g, 7.80 mmol) in DMF (10 mL) was added to a suspension of NaH (550 mg, 60% in oil) in DMF (25 ml) at 0∞C. After 15 minutes n-Bu$_4$NI (1.94 g, 5.30 mmol) was added followed by chlorocyclopentanone (1.66 g, 14.0 mmol) after another 20 minutes. The mixture was allowed to warm to room temperature and stirred for 16 h. The dark solution was poured into 10% aq. HCl (150 mL) and extracted with EtOAc (5×30 mL). The combined organic layers were washed with sat. aq. NaHCO$_3$, and brine, and dried over MgSO$_4$. Evaporation of solvent and chromatography on silica gel using toluene/EtOAc (4:1) gave the title compound (2.1 g, 74%) m.p. 156–157∞C., MS m/z 365 (M+H)$^+$.

EXAMPLE 25

3-((2,2-Difluorocyclopentyl)oxy-5,5-dimethyl-4-(4-methylsulfonyl-phenyl)-5.5-furan-2-one To a solution of the ketone from Example 24 (1.03 g, 2.83 mmol) in 1,2-dichloroethane (10 mL) was added DAST (2.28 g, 14.1 mmol, 1.87 mL). The solution was warmed to 45∞C. for 2 h, cooled and diluted with dichloromethane (50 mL), and washed with 10% aq. HCl, sat. aq. NaHCO$_3$ and brine. After drying over MgSO$_4$, evaporation of the solvent and silica gel chromatography using toluene (EtOAc (4:1) the product was obtained as a colorless powder, 749 mg (69%), mp 126–127∞C., MS m/z 387 (M+H)$^+$.

What is claimed is:

1. A compound of Formula I

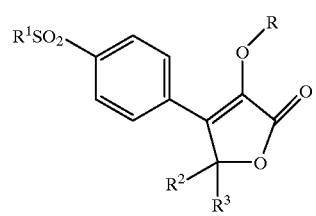

wherein:
R is a mono-, di- or tri-substituted C$_{1-12}$alkyl, or an unsubstituted or mono-, di- or tri-substituted linear or branched C$_{2-10}$alkenyl, or an unsubstituted or mono-, di- or tri-substituted linear or branched C$_{2-10}$alkynyl, or an unsubstituted or mono-, di- or tri-substituted $C_{3-12}$cycloalkenyl, or an unsubstituted or mono-, di- or tri-substituted $C_{5-12}$cycloalkynyl, wherein the substituents are chosen from the group consisting of
(a) halo, selected from F, Cl, Br, and I,
(b) OH,
(c) $CF_3$,
(d) $C_{3-6}$cycloalkyl,
(e) =O,
(f) dioxolane,
(g) CN and $R^1$ is selected from the group consisting of
(a) $CH_3$,
(b) $NH_2$,
(c) $NHC(O)CF_3$,
(d) $NHCH_3$;

$R^2$ and $R^3$ are independently chosen from the group consisting of
(a) hydrogen,
(b) $C_{1-10}$alkyl, or $R^2$ and $R^3$ together with the carbon to which they are attached form a saturated monocyclic carbon ring of 3, 4, 5, 6 or 7 atoms.

2. A compound according to claim 1 wherein $R^2$ and $R_3$ are each independently methyl.

3. A compound according to claim 1 wherein $R^1$ is $CH_3$ or $NH_2$.

4. A compound according to claim 1 wherein R is a mono-, di- or tri-substituted $C_{1-10}$alkyl, wherein the substituents are selected from hydroxy, F, Cl and Br.

5. A compound according to claim 1 wherein $R^1$ is selected from the group consisting of
(a) $CH_3$,
(b) $NH_2$, R is a mono-, di- or tri-substituted $C_{1-6}$alkyl, or an unsubstituted or mono-, di- or tri-substituted linear or branched $C_{2-6}$alkenyl, or an unsubstituted or mono-, di- or tri-substituted linear or branched $C_{2-6}$alkynyl, or an unsubstituted or mono-, di- or tri-substituted $C_{3-6}$cycloalkenyl, or an unsubstituted or mono-, di- or tri-substituted $C_{5-8}$cycloalkynyl, wherein the substituents are chosen from the group consisting of
(a) halo, selected from Cl, Br, and F,
(b) OH,
(c) $CF_3$,
(d) CN and $R^2$ and $R^3$ are each independently methyl.

6. A compound according to claim 1 wherein $R^1$ is selected from the group consisting of
(a) $CH_3$,
(b) $NH_2$, R is a mono-, di- or tri-substituted $C_{1-4}$alkyl, or an unsubstituted or mono-, di- or tri-substituted linear or branched $C_{2-4}$alkenyl wherein the substituents are chosen from the group consisting of
(a) halo, selected from Cl, Br, and F,
(b) OH,
(c) $CF_3$,
(d) CN and $R^2$ and $R^3$ are each independently methyl.

7. A compound according to claim 1 wherein $R^1$ is selected from the group consisting of
(a) $CH_3$, R is a mono-, di- or tri-substituted $C_{1-4}$alkyl, linear wherein the substituents are chosen from the group consisting of (a) halo, selected from Cl, Br, and F,
(b) OH,
(c) $CF_3$,
(d) CN and $R^2$ and $R^3$ are each independently methyl.

8. A compound according to claim 1 selected from the group consisting of (1) 5,5-Dimethyl-3-((1-methylallyl)oxy)-4-(4-methylsulfonylphenyl)-5H-furan-2-one, (2) 5,5-Dimethyl-3-(1,1,1,3,3,3-hexafluoropropoxy)-4-(4-methylsulfonylphenyl)-5H-furan-2-one, (3) 5,5-Dimethyl-3-((1-methyl-2-propynyl)oxy)-4-(4-methylsulfonylphenyl)-5H-furan-2-one, (4) 3-((1R,2S)-(1S, 2R)-2-hydroxy-1-methylpropyl)oxy)-5,5-dimethyl-4-(4-methylsulfonylphenyl)-5H-furan-2-one, (5) 3-((2-hydroxy-2-methyl-3-butenyl)oxy)-5,5-dimethyl-4-(4-methylsulfonyl)phenyl-5H-furan-2-one, (6) 3-(2-Bromo-1-methylethoxy)-5,5-dimethyl-4-(4-methylsulfonylphenyl)-5H-furan-2-one, (7) 3-(Isopropenyloxy)-5,5-dimethyl-4-(4-methylsulfonylphenyl)-5H-furan-2-one, (8) 3-(((2S)-3-hydroxy-2-methylpropyl)oxy)-5,5-dimethyl-4(4-methylsulfonylphenyl)-5H-furan-2-one, (9) 3-(((2R)-3-hydroxy-2-methylpropyl)oxy)-5,5-dimethyl-4-(4-methylsulfonylphenyl)-5H-furan-2-one,

(10) 3-(((2R)-3-Fluoro-2-methylpropyl)oxy)-5,5-dimethyl-4-(4-methylsulfonylphenyl)-5H-furan-2-one,

(11) 3-(((2S)-3-fluoro-2-methylpropyl)oxy)-5,5-dimethyl-4-(4-methylsulfonylphenyl)-5H-furan-2-one,

(12) 3-(2-Hydroxy-1-methylethoxy)-5,5-dimethyl-4-(4-methylsulfonylphenyl)-5H-furan-2-one,

(13) 3-(2-Fluoro-1-methylethoxy)-5,5-dimethyl-4-(4-methylsulfonylphenyl)-5H-furan-2-one,

(14) 5,5-Dimethyl-4-(4-methylsulfonylphenyl)3-(2-propynyloxy)-5H-furan-2-one,

(15) 3-(Allyloxy)-5,5-dimethyl-4-(4-methylsulfonylphenyl)-5H-furan-2-one,

(16) 3-(1,4-dioxaspiro[4,5]dec-8-yloxy)-5,5-dimethyl-4-(4-methylsulfonylphenyl)-5H-furan-2-one,

(17) 3-[(4,4-difluorocyclohexyl)oxy]-5,5-dimethyl-4(4-(methylsulfonylphenyl)-5H-furan-2-one,

(18) 5,5-dimethyl-3-(2-methylallyloxy)-4-(4-(methylsulfonylphenyl)-5H-furan-2-one,

(19) 5,5-Dimethyl-3-[(1-methylcyclopropyl)methoxy]-4-(4-methylsulfonylphenyl)-5H-furan-2-one,

(20) 3-{[2-(fluoromethyl)allyl]oxy}-5,5-dimethyl-4-(4-methylsulfonylphenyl)-5H-furan-2-one,

(21) 3-{[1-(hydroxymethyl)cyclopropyl]methoxy}-5,5-dimethyl-4-(4-methylsulfonylphenyl)-2-5H-furan-2-one,

(22) 3-[(1-fluorocyclobutyl)methoxy]-5,5-dimethyl-4-(4-methylsulfonylphenyl)-5H-furan-2-one,

(23) 3-{[1-(fluoromethyl)cyclopropyl]methoxy}-5,5-dimethyl-4-(4-methylsulfonylphenyl)-5H-furan-2-one,

(24) 3-((2-oxocyclopentyl)oxy)-5,5-dimethyl-4-(4-methylsulfonylphenyl)-5H-furan-2-one, and

(25) 3-((2,2-difluorocyclopentyl)oxy-5,5-dimethyl-4-(4-methylsulfonylphenyl)-5,5-furan-2-one.

9. A pharmaceutical composition for treating an inflammatory disease susceptible to treatment with an non-steroidal anti-inflammatory agent comprising:

a non-toxic therapeutically effective amount of a compound according to claim 1 and a pharmaceutically acceptable carrier.

10. A pharmaceutical composition for treating cyclooxygenase mediated diseases treated by an active agent that selectively inhibits COX-2 in preference to COX-1 comprising:

a non-toxic therapeutically effective amount of a compound according to claim 1 and a pharmaceutically acceptable carrier.

11. A method of treating an inflammatory disease susceptible to treatment with an non-steroidal anti-inflammatory agent comprising:

administration to a patient in need of such treatment of a non-toxic therapeutically effective amount of a compound according to claim 1 and a pharmaceutically acceptable carrier.

12. A method of treating cyclooxygenase mediated diseases treated by an active agent that selectively inhibits COX-2 in preference to COX-1 comprising:

administration to a patient in need of such treatment of a non-toxic therapeutically effective amount of a compound according to claim 1.

13. A pharmaceutical composition comprising a compound of claim 1 and a pharmaceutically acceptable carrier.

\* \* \* \* \*